US010844411B2

(12) United States Patent
Conte et al.

(10) Patent No.: US 10,844,411 B2
(45) Date of Patent: Nov. 24, 2020

(54) INHIBITORS OF STEROL METABOLISM FOR THEIR USE TO ACCUMULATE TRIGLYCERIDES IN MICROALGAE, AND METHODS THEREOF

(71) Applicants: Commissariat A L'energie Atomique Et Aux Energies Alternatives, Paris (FR); Centre National de la Recherche Scientifique, Paris (FR)

(72) Inventors: Melissa Conte, Grenoble (FR); Lina-Juana Dolch, Grenoble (FR); Coline Mei, Grenoble (FR); Caroline Barette, Sassenage (FR); Dimitris Petroutsos, Grenoble (FR); Denis Falconet, Eybens (FR); Juliette Jouhet, Seyssinet (FR); Fabrice Rebeille, Voreppe (FR); Jean-Christophe Cintrat, Igny (FR); Eric Marechal, Grenoble (FR)

(73) Assignees: Commissariat A L'Energie Atomique Et Aux Energies Alternatives, Paris (FR); Centre National De La Recherche Scientifique, Paris (FR)

( * ) Notice: Subject to any disclaimer, the term of this patent is extended or adjusted under 35 U.S.C. 154(b) by 20 days.

(21) Appl. No.: 15/112,886

(22) PCT Filed: Jan. 27, 2015

(86) PCT No.: PCT/IB2015/050614
§ 371 (c)(1),
(2) Date: Jul. 20, 2016

(87) PCT Pub. No.: WO2015/111029
PCT Pub. Date: Jul. 30, 2015

(65) Prior Publication Data
US 2016/0348138 A1 Dec. 1, 2016

(30) Foreign Application Priority Data
Jan. 27, 2014 (EP) .................................... 14305111

(51) Int. Cl.
*C12P 7/64* (2006.01)
*A23L 33/12* (2016.01)
*C10L 1/02* (2006.01)

(52) U.S. Cl.
CPC ............ *C12P 7/6463* (2013.01); *A23L 33/12* (2016.08); *C10L 1/02* (2013.01); *C12P 7/649* (2013.01); *A23V 2002/00* (2013.01); *C10L 2200/0469* (2013.01); *C10L 2290/26* (2013.01); *C10L 2290/544* (2013.01); *Y02E 50/13* (2013.01)

(58) Field of Classification Search
None
See application file for complete search history.

(56) References Cited

U.S. PATENT DOCUMENTS 8,778,643 B2 * 7/2014 Franz ....................... C12N 1/12
435/134

FOREIGN PATENT DOCUMENTS

KR 2012086940 * 8/2012
WO WO 2013/138523 9/2013

OTHER PUBLICATIONS

Lai et al . "Biotransformation and Bioconcentration of steroid estrogens by Chlorella vulgaris". Applied and Environmental Microbiology. Feb. 2002, vol. 68, No. 2, pp. 859-864.*
Ying Liu et al. "Cellular responses, biodegradation and bioaccumulation of endocrine disrupting chemicals in marine diatom *Navicula incerta*". Chemosphere 2010, 80, pp. 592-599.*
A.K. Franz et al., "Phenotypic Screening with Oleaginous Microalgae Reveals Modulators of Lipid Productivity," ACS Chemical Biology, vol. 8, 2013, pp. 1053-1062.
Wei-Luen Yu et al., "Modifications of the metabolic pathways of lipid and triacylglycerol production in microalgae," Microbial Cell Factories, Biomed Central, London, NL, vol. 10, No. 1, Nov. 2, 2011, p. 91.
Emily M. Trentacoste et al., "Metabolic engineering of lipid catabolism increases microalgal lipid accumulation without comprising growth," Proceedings of the National Academy of Sciences, vol. 110, No. 49, Nov. 18, 2013, pp. 19748-19753.
Yusuf Chisti, "Biodiesel from microalgae beats bioethanol," Trends in Biotechnology, vol. 26, No. 3, Jan. 24, 2008, pp. 126-131.
Xiaodong Deng et al., "Effect of the expression and knockdown of citrate synthase gene on carbon flux during triacylglycerol biosynthesis by green algae *Chlamydomonas reinhardtii*," BMC Biochemistry, Biomed Central, vol. 14, No. 1, Dec. 30, 2013, p. 38.
International Search Report and Written Opinion from International Application No. PCT/IB2015/050614, dated Apr. 8, 2015.

(Continued)

*Primary Examiner* — Vera Afremova
(74) *Attorney, Agent, or Firm* — Alston & Bird LLP

(57) ABSTRACT

The invention relates to a method for accumulating triacylglycerols in microalgae by inhibiting the sterol metabolism, by incubating the microalgae with an inhibitor of sterol metabolism. The invention also relates to a method for producing fatty acids, biofuels, pharmaceutical or cosmetic compositions, and also food supplements, comprising a triacylglycerols accumulation step in microalgae according to the invention. Finally, the invention concerns the use of an inhibitor of sterol metabolism to accumulate triglycerides in microorganisms, and preferably microalgae.

7 Claims, 7 Drawing Sheets

(56) References Cited

OTHER PUBLICATIONS

Belter, A. et al., Squalene Monoxygenase—A Target for Hypercholesterolemic Therapy, Biol. Chem., vol. 392 (Dec. 2011) 1053-1075.
Berman, J. D. et al., Effects of Ketoconazole on Sterol Biosynthesis by Leishmania Mexicana, Mexicana Amastigotes in Murine Macrophase Tumor Cells, Molecular and Biochemical Parasitology, 20 (1986) 85-92.
Office Action for European Application No. 14305111.8 dated Nov. 23, 2018, 3 pages.

* cited by examiner

INHIBITORS OF STEROL METABOLISM FOR THEIR USE TO ACCUMULATE TRIGLYCERIDES IN MICROALGAE, AND METHODS THEREOF

FIELD

The invention relates to a method for accumulating triacylglycerols in microalgae by inhibiting the sterol metabolism. The invention also relates to a method for producing fatty acids, biofuels, pharmaceutical or cosmetic compositions, and also food supplements, comprising a triacylglycerols accumulation step in microalgae according to the invention. Finally, the invention concerns the use of an inhibitor of sterol metabolism to accumulate triglycerides in microorganisms, and preferably microalgae.

BACKGROUND

It is acknowledged that oilseed production from crops cannot be diverted from nutritional purpose (Durrett et al., The Plant Journal (2008) 54, 593-607). Therefore, efforts are directed towards the oil production in other organisms like algae (Chisti, Biotechnology Advances 25 (2007) 294-306; Chisti, Trends in Biotechnology, 2008, Vol 26, No. 3; Dismukes et al., Current Opinion in Biotechnology 2008, 19:235-240; Scott et al., Current Opinion in Biotechnology 2010, 21:277-286; Singh et al., Bioresource Technology 102 (2011) 26-34). Studies undergone on triacylglycerol (TAG, also called oil) production in algae (Table 1 below) have focused on the increase of TAG in cytosolic droplets.

TABLE 1

Oil content of some algae (from Chisti, Biotechnology Advances 25 (2007) 294-306)

| Microalga | Oil content (% dry wt) |
|---|---|
| Botryococcus braunii | 25-75 |
| Chlorella sp. | 28-32 |
| Crypthecodinium cohnii | 20 |
| Cylindrotheca sp. | 16-37 |
| Dunaliella primolecta | 23 |
| Isochrysis sp. | 25-33 |
| Monallanthus salina | >20 |
| Nannochloris sp. | 20-35 |
| Nannochloropsis sp. | 31-68 |
| Neochloris oleoabundans | 35-54 |
| Nitzschia sp. | 45-47 |
| Phaeodactylum tricornutum | 20-30 |
| Schizochytrium sp. | 50-77 |
| Tetraselmis sueica | 15-23 |

The advantages of microalgae over land plants have been summarized in the EPOBIO report (Micro- and macro-algae: utility for industrial application, September 2007, Editor: Dianna Bowles). Both plants (crops) cultivable on arable lands and microalgae grown in open ponds or in confined reactors are potential sources of TAG and fatty acids for industrial purposes and biofuels (Dismukes et al., Current Opinion in Biotechnology 2008, 19:235-240). However, serious concerns have been raised by the intensive agricultural practices the use of crops implies and the diversion of crops from food to non-food chains. Efforts are thus needed to develop novel generation biofuels based on photosynthetic microorganisms.

The main advantages of microalgae in relation to plants for the production of TAG are the following:

This bioresource does not compete with the agro-resources used for animal or human nutrition.

Algal growth can be monitored in controlled and confined conditions in an environmental friendly process using recycled inorganic and organic wastes generated by other human activities and the use of microalgae allows trapping and converting industrial byproduct gases (e.g. $CO_2$) into valuable organic molecules (Chisti, Biotechnology Advances 25 (2007) 294-306; Chisti, Trends in Biotechnology, 2008, Vol 26, No. 3; Chisti, Journal of Biotechnology 167 (2013) 201-214).

The algal biomass productivity is high, microalgae showing a very high potential of productivity with cost savings when compared to land plants (see Table 2). Their yield is variable and determined by the culturing approach employed: it is relatively low in open pond systems while it can be significantly increased in closed photobioreactors where culture parameters can be controlled.

This bioresource does not depend on a geographical location, or on a season.

TABLE 2

Comparison of biomass productivity of major crops ("C3" or "C4" type photosynthesis) and microalgae (extract from the « EPOBIO project » report, University of York (September 2007), Table 4).

| | Microalgae | "C4" crops (sorghum, maize, sugarcane . . . ) | "C3" crops (wheat, sunflower . . . ) |
|---|---|---|---|
| Maximal productivity ($T \cdot ha^{-1} \cdot y^{-1}$) | | | |
| Microalgae (photobioreactors) | 130 to 150 | — | — |
| Higher plants (maximum productivity) | — | 72 | 30 |
| Average productivity in production systems ($T \cdot ha^{-1} \cdot y^{-1}$) | | | |
| Microalgae (large scale) | 10 to 50 | — | — |
| Higher plants (field) | — | 10 to 30 | 8 to 18 |
| Biomass production costs ($USD \cdot kg^{-1}$) | 0.4-40 | 0.04 | 0.04 |

The economic viability of this sector of bioindustry is challenged by the current limitation to combine the overall biomass yield, i.e. dry weight of algal organic matter produced per liter and the proportion of valuable molecules, i.e. sufficiently high proportion of TAG per dry weight for industrial extraction and processing (Chisti, Biotechnology Advances 25 (2007) 294-306; Chisti, Trends in Biotechnology, 2008, Vol 26, No. 3; Chisti, Journal of Biotechnology 167 (2013) 201-214).

In particular, the lipid composition of microalgae is compatible with biodiesel production (Dismukes et al., Current Opinion in Biotechnology 2008, 19:235-240; Scott et al., Current Opinion in Biotechnology 2010, 21:277-286). The rationale for producing biodiesel from microalgae is to use sunlight to convert water and carbon dioxide into biomass. This biomass is then specifically redirected towards the synthesis of oil for the generation biofuels, by applying external stimuli like nutrient stresses, and/or by genetic engineering of metabolism (Dorval Courchesne et al., Journal of Biotechnology 141 (2009) 31-41).

The three most important classes of micro-algae in terms of abundance are the diatoms (Bacillariophyceae), the green algae (Chlorophyceae), and the golden algae (Chrysophyceae) (EPOBIO definition). Diatoms are a major phylum of the phytoplankton biodiversity in oceans, fresh water and various soil habitats. They are responsible for up to 25% of the global primary productivity. Study of this group of eukaryotes has benefited from recent developments on *Phaeodactylum tricornutum*, a model of pennate diatoms. Diatoms, like other microalgae, are considered a plausible alternative source of hydrocarbons to replace fossil fuels or chemicals from petrochemistry, with the advantage of having a neutral $CO_2$ balance, based on the hypotheses that $CO_2$ and water can be efficiently converted into biomass by photosynthesis and that the carbon metabolism could be controlled so that they accumulate energetically-rich TAG. Different phytoplanktonic organisms of the Chromalevolata superphylum have focused the attention for their ability to accumulate TAG, with promising initial yields and appropriate robustness and physical properties to be implemented in an industrial process, including *Phaeodactylum tricornutum*. *Phaeodaetylum tricornutum* is currently used for the industrial production of omega-3 polyunsaturated fatty acids but industrial implementation for this application and for other applications such as biofuels is still limited by the growth retardation and low yield in biomass when TAG accumulation is triggered using conventional nutrient starvation approaches, such as nitrogen starvation (Chisti, Journal of Biotechnology 167 (2013) 201-214). These approaches have an important drawback which is the limitation of growth that the nitrogen starvation induces. *Phaeodactylum tricornutum* exhibits interesting properties for an industrial implementation, like the ability to grow in the absence of silicon or the sedimentation of cells that could be useful for harvesting techniques. Attempts to promote TAG accumulation can rely on various strategies that can be combined, including the stimulation of fatty acid and TAG biosynthesis, the blocking of pathways that diverts carbon to alternative metabolic routes and eventually the arrest of TAG catabolism. Small molecules could act on each of these three aspects of TAG metabolism.

It is possible to promote the accumulation of oil in microorganisms by inhibiting or blocking metabolic pathways that direct the carbon fluxes to alternative metabolites. For instance, it is well known that blocking the accumulation of carbohydrate in storage sugars such as starch, promotes the accumulation of oils (Siaut et al., BMC Biotechnology 2011, 11:7).

However, there remains a need for alternative methods to trigger the accumulation of oil when algae are grown in a nitrogen-rich medium, and by trying to avoid blocking carbohydrate storage metabolism. Indeed, the carbohydrates produced after $CO_2$ photosynthetic conversion serve as a source of carbon for all other organic molecules within the cell, so blocking their storage has a very strong negative impact on cell growth. Other metabolic pathways using carbon might be blocked and allow a redirection of carbon metabolism towards TAG metabolism.

SUMMARY

In this aim, the Inventors have now identified that the metabolism of sterols is an alternative sink of carbon, its inhibition in microalgae triggering the accumulation of oils.

Therefore, a first subject of the invention is a method for triggering TAG accumulation in microalgae by inhibiting the sterol metabolism, preferably by inhibiting the synthesis of the sterols, said method overcoming the disadvantages listed above by incubating the microalgae with an inhibitor of sterol metabolism.

Within the framework of the invention, the term microalgae refers to microalgae for eukaryotes.

Also in the sense of the present invention, the TAG is built by esterification of a 3-carbon glycerol backbone at positions 1, 2 and 3 by fatty acids. Below, TAG is synthesized by esterification of a glycerol backbone by three fatty acids ($R_1$, $R_2$, $R_3$).

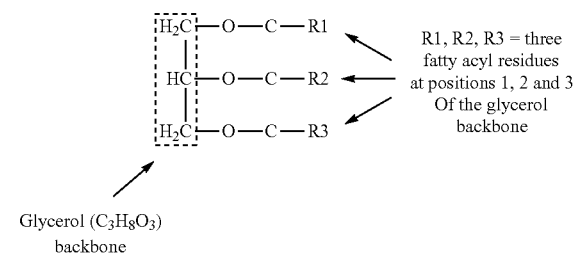

Glycerol ($C_3H_8O_3$) backbone

In the sense of the present invention:

Alkyl groups are chosen among ($C_1$-$C_{26}$)alkyl groups, preferably ($C_1$-$C_{18}$)alkyl groups, and more preferably ($C_1$-$C_6$)alkyl groups such as methyl, ethyl, n-propyl, isopropyl, n-butyl, sec-butyl, tert-butyl and isobutyl radicals;

Alkenyl groups are chosen among hydrocarbon chains of 2 to 26 carbon atoms, preferably 2 to 18, and more preferably 1 to 6, having at least one carbon-carbon double bond. Examples of alkenyl groups include ethenyl, propenyl, isopropenyl, 2,4-pentadienyl;

Alkynyl groups are chosen among hydrocarbon chains of 2 to 26 carbon atoms, preferably 2 to 18, and more preferably 1 to 6, having at least one carbon-carbon triple bond;

Alkylalkenyl means any group derived from an alkenyl group as defined above wherein a hydrogen atom is replaced by an alkyl group;

Alkynylalkenyl means any group derived from an alkenyl group as defined above wherein a hydrogen atom is replaced by an alkynyl group;

Cycloalkyl groups refer to a monovalent cyclic hydrocarbon radical preferably of 3 to 7 ring carbons. The cycloalkyl group can have one or more double bonds and can optionally be substituted. The term "cycloalkyl" includes, for examples, cyclopropyl, cyclohexyl, cyclohexenyl and the like;

Heteroalkyl groups mean alkyl groups as defined above in which one or more hydrogen atoms to any carbon of the alkyl is replaced by a heteroatom selected from the group consisting of N, O, P, B, S, Si, Sb, Al, Sn, As, Se and Ge. The bond between the carbon atom and the heteroatom may be a single or a double bond. Suitable heteroalkyl groups include cyano, benzoyl, methoxy, acetamide, borates, sulfones, sulfates, thianes, phosphates, phosphonates, and the like;

Alkoxy groups are chosen among ($C_1$-$C_{20}$)alkoxy groups, and preferably ($C_1$-$C_4$)alkoxy groups such as methyloxy, ethyloxy, n-propyloxy, iso-propyloxy, n-butyloxy, sec-butyloxy, tert-butyloxy and isobutyloxy radicals;

Aryl groups means any functional group or substituent derived from at least one simple aromatic ring; an aromatic ring corresponding to any planar cyclic compound having a delocalized π system in which each atom of the ring comprises a p-orbital, said p-orbitals overlapping themselves. More specifically, the term aryl includes, but is not limited to, phenyl, biphenyl, 1-naphthyl, 2-naphthyl, anthracyl, pyrenyl, and the substituted forms thereof;

Heteroaryl groups means any functional group or substituent derived from at least one aromatic ring as defined above and containing at least one hetero atom selected from P, S, O and N. The term heteroaryl includes, but is not limited to, furan, pyridine, pyrrole, thiophene, imidazole, pyrazole, oxazole, isoxazole, thiazole, isothiazole, tetrazole, pyridazole, pyridine, pyrazine, pyrimidine, pyridazine, benzofurane, isobenzofurane, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine. The aryl and heteroaryl groups of the invention comprise preferably 1 to 12 carbon atoms, and more preferably 5 or 6 carbon atoms;

Arylalkyl means any group derived from an alkyl group as defined above wherein a hydrogen atom is replaced by an aryl or a heteroaryl group;

Arylalkenyl means any group derived from an alkenyl group as defined above wherein a hydrogen atom is replaced by an aryl or a heteroaryl group;

Arylalkynyl means any group derived from an alkynyl group as defined above wherein a hydrogen atom is replaced by an aryl or a heteroaryl group;

Alkylaryl means any group derived from an aryl group as defined above wherein a hydrogen atom is replaced by an alkyl group.

According to the invention, halogen atoms are chosen among bromine, chlorine, fluorine and iodine, and preferably bromine, chlorine and fluorine.

The acid addition salts of the inhibitor of sterol metabolism according to the invention may be for example chosen among hydrochloride, hydrobromide, sulphate or bisulphate, phosphate or hydrogenophosphate, acetate, benzoate, succinate, fumarate, maleate, lactate, citrate, tartrate, gluconate, methanesulphonate, benzene-sulphonate and para-toluene-sulphonate.

According to a preferred embodiment, in the method of the invention the inhibition of the sterol metabolism is realized by incubating the microalgae with an inhibitor of sterol metabolism in a nitrogen medium.

The concentration of the inhibitor of sterol metabolism may range from 1 µM to 1 M, and preferably from 5 to 20 µM. The incubation step lasts preferably from 24 to 72 hours.

The microalgae of the invention is advantageously selected from microalgae of the diatom phylum, the Chromalveolata phylum, and the Archaeplastidae phylum, and more advantageously from microalgae of the diatom phylum and the Chromalveolata phylum. Preferably, the microalgae is selected from the diatom micro-algae species *Phaeodactylum tricornutum* and *Thalassiosira pseudonana*, the Chromalveolata micro-algae species *Nannochloropsis*, and more preferably *Nannochloropsis gaditana*, *Nannochloropsis oceanica*, *Nannochloropsis salina*, and the Archaeplastidae micro-algae species *Chlamydomonas, Ostreococcus, Chlorella*. More preferably, the microalgae is selected from the diatom micro-algae species *Phaeodactylum tricornutum* and *Thalassiosira pseudonana*, and the Chromalveolata micro-algae species *Nannochloropsis*, and more preferably *Nannochloropsis gaditana*, *Nannochloropsis oceanica*, *Nannochloropsis salina*.

Sterol inhibitors consist of molecules that have an effect on any protein activity in the biosynthesis of sterols, a pathway that starts with the biosynthesis of HMG-CoA reductase, followed by the biosynthesis of mevalonic acid, epoxysqualene and then all steroid structures deriving from epoxysqualene (see FIG. 1). The identification of compounds which inhibit sterol metabolism, preferably with at least a decrease of 20% of total sterol content per cell, can be achieved simply by colorimetric or fluorometric dosage methods such as that commercialized by CellBioLabs (Total Sterol Assay Kit, Colorimetric method, reference STA-384 or Fluorometric method, reference STA-390), based on a treatment by cholesterol oxidase/esterase, which has proved to be efficient on detecting plant sterols (D. Kritchevsky and S. A. Tepper, Clinical Chemistry, Vol. 25, No. 8, 1464-1465 (1979)), or also according to methods such as those exemplified in the applications WO 2010/046385 and WO 97/03202.

According to an embodiment of the invention, the inhibitor of sterol metabolism is a compound of formula (I) or a salt thereof:

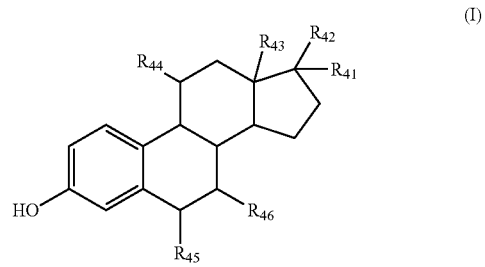

(I)

wherein:

$R_{41}$ and $R_{42}$, identical or different, represent a hydrogen atom, alkyl, alkenyl, alkynyl, or hydroxyl, —$COR_{4a}$ or —$COOR_{4a}$ group, in which $R_{4a}$ represents a hydrogen atom, linear or branched alkyl, aryl, heteroaryl group, optionally substituted with one or more groups independently selected from alkyl or cycloalkyl groups, preferably $C_4$-$C_6$ cycloalkyl groups, or $R_{41}$ and $R_{42}$ form together an oxygen atom attached by a double bond;

$R_{43}$ represents a hydrogen atom, or an alkyl group, preferably $C_1$-$C_3$ alkyl group; and $R_{44}$, $R_{45}$ and $R_{46}$, identical or different, represent a hydrogen atom, alkyl, alkoxy, hydroxyl group, or an oxygen atom attached by a double bond, said alkyl group being optionally substituted with one or more halogen atoms, and including optionally in its chain one or more sulfoxide functions.

Advantageously, $R_{41}$ and $R_{42}$, identical or different, represent a hydrogen atom, a nitrile, hydroxyl, $C_1$-$C_2$ alkyl or —$COOR_{4a}$ group in which $R_{4a}$ is in $C_1$-$C_7$ and is optionally substituted by a $C_4$-$C_6$ cycloalkyl group, or $R_{41}$ and $R_{42}$ form together an oxygen atom attached by a double bond.

According to another embodiment of the invention, the inhibitor of sterol metabolism is a compound of formula (II) or a salt thereof:

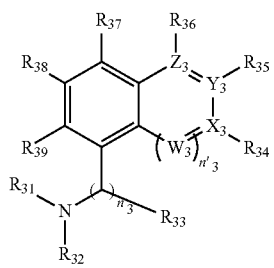

(II)

wherein:
- $W_3$, $X_3$, $Y_3$ and $Z_3$ represent carbon, sulphur, nitrogen or oxygen atom, and preferably $W_3$, $X_3$, $Y_3$ and $Z_3$ represent carbon atoms;
- $n_3$ and $n_{3'}$, independently, are integer equal to 0 or 1, and preferably $n_3$ and $n_{3'}$ are equal to 1;
- $R_{31}$ and $R_{32}$, identical or different, represent a hydrogen atom, linear or branched alkyl, alkenyl, alkynyl, alkylalkenyl, alkynylalkenyl, cycloalkyl, alkylaryl, arylalkyl, and preferably a benzyl group, arylalkenyl, arylalkynyl, heteroalkyl, heteroaryl groups, or form together a cycloalkyl group comprising 5 to 6 carbon atoms, one or two carbon atoms of said cycloalkyl group being possibly replaced by one or two heteroatoms, preferably nitrogen atoms, or one of $R_{31}$ or $R_{32}$ form together with $R_{39}$ a cycloalkyl group comprising 5 to 6 carbon atoms, one or two carbon atoms of said cycloalkyl group being possibly replaced by one or two heteroatoms, preferably oxygen atoms, said $R_{31}$ or $R_{32}$ being optionally substituted with one or more groups independently selected from linear or branched alkyl, cycloalkyl such as

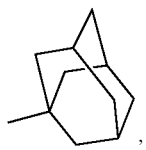

alkynyl, said alkynyl group being preferably a $C_5$-$C_{12}$ branched alkynyl group, arylalkyl, aryl, heteroaryl, hydroxyl, halogen, nitro, —$COR_{3a}$ or —$NR_{3a}R_{3b}$ group, in which $R_{3a}$ and $R_{3b}$, identical or different, represent a hydrogen atom or a linear or branched alkyl chain;
- $R_{33}$ represents a hydrogen atom, a linear or branched alkyl chain such as a $C_1$-$C_3$ alkyl group, or a nitrile group, and preferably $R_{33}$ represents a hydrogen atom;
- $R_{34}$, $R_{35}$, $R_{36}$, $R_{37}$, $R_{38}$ and $R_{39}$, identical or different, represent hydrogen or halogen atoms, or hydroxyl groups, and preferably $R_{34}$, $R_{35}$, $R_{36}$, $R_{37}$, $R_{38}$ and $R_{39}$ are hydrogen atoms.

The dotted lines of formula (II) represent single or double bonds. Specifically, said $W_3$—$X_3$ bond or $Y_3$—$Z_3$ bond is single bond respectively when one of $W_3$ or $X_3$ of the $W_3$—$X_3$ bond, or one of $Y_3$ or $Z_3$ of the $Y_3$—$Z_3$ bond, is sulphur or oxygen. Said $W_3$—$X_3$ bond or $Y_3$—$Z_3$ bond is double bond respectively when $W_3$ and $X_3$, or $Y_3$ and $Z_3$ are carbon or nitrogen.

According to a preferred embodiment, $R_{31}$ and $R_{32}$, identical or different, represent a hydrogen atom, linear or branched alkyl, alkenyl, alkynyl, alkynylalkenyl, cycloalkyl, alkylaryl, arylalkyl, and preferably a benzyl group, arylalkenyl, arylalkynyl, heteroalkyl, heteroaryl groups, or form together a cycloalkyl group comprising 5 to 6 carbon atoms, one or two carbon atoms of said cycloalkyl group being possibly replaced by one or two heteroatoms, preferably nitrogen atoms, or one of $R_{31}$ or $R_{32}$ form together with $R_{39}$ a cycloalkyl group comprising 5 to 6 carbon atoms, one or two carbon atoms of said cycloalkyl group being possibly replaced by one or two heteroatoms, preferably oxygen atoms, said $R_{31}$ or $R_{32}$ being optionally substituted with one or more groups independently selected from linear or branched alkyl, cycloalkyl such as

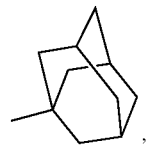

alkynyl, said alkynyl group being preferably a $C_5$-$C_{12}$ branched alkynyl group, arylalkyl, aryl, heteroaryl, hydroxyl, halogen, nitro, —$COR_{3a}$ or —$NR_{3a}R_{3b}$ group, in which $R_{3a}$ and $R_{3b}$, identical or different, represent a hydrogen atom or a linear or branched alkyl chain.

According to a more preferred embodiment, $R_{31}$ and $R_{32}$, identical or different, represent $C_1$-$C_6$ linear or branched alkyl chains, or an arylalkyl group, optionally substituted with one or more groups independently selected from linear or branched alkyl. Advantageously, $R_{31}$ represents a $C_1$-$C_6$ linear or branched alkyl chain, and $R_{32}$ a benzyl group substituted with a $C_1$-$C_6$ linear or branched alkyl chain, or an alkenyl group substituted with a linear or branched alkynyl group, such as a —$(CH_2)n_{3''}$-CH=CH—C≡C—C$(CH_3)_3$ group in which $n_{3''}$ ranges from 1 to 6.

According to another embodiment of the invention, the inhibitor of sterol metabolism is a compound of formula (III) or a salt thereof:

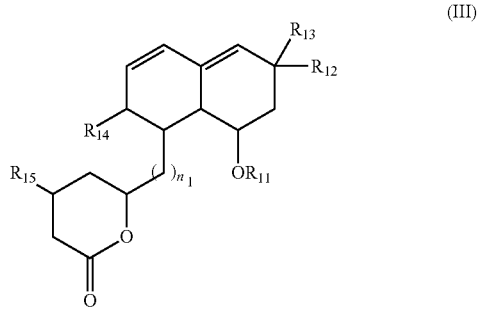

(III)

wherein:
- $n_1$ ranges from 1 to 12, and preferably $n_1$=2,
- $R_{11}$ represents a hydrogen atom; a —$COR_{1a}$ group, in which $R_{1a}$ is a group selected from a linear or branched alkyl chain, optionally substituted with one or more groups independently selected from hydroxyl, halogen, nitro, optionally substituted benzyl groups, or optionally substituted aryl groups such as phenyl groups, said aryl groups being eventually substituted with one or more groups independently selected from halogen atoms and methyl groups;
- $R_{12}$, $R_{13}$ and $R_{14}$, identical or different, represent a hydrogen atom; a linear or branched alkyl chain; a hydroxyl group; a —$CH_2OH$ group; a —$COOR_{1b}$ group, in which $R_{1b}$ represents a hydrogen atom, or a linear or branched alkyl chain; a —$OSiR_{1c}R_{1d}R_{1e}$ group, in which $R_{1c}$, $R_{1d}$ and $R_{1e}$, identical or different, represent a hydrogen atom, or a linear or branched alkyl chain; or $R_{12}$ and $R_{13}$ are fused together to form an exo methylene group;

$R_{15}$ represents a hydroxyl group; a —$OSiR_{1c}R_{1d}R_{1e}$ group as defined above; a —$COOR_{1f}$ group, in which $R_{1f}$ represents a hydrogen atom, or a linear or branched alkyl chain; a —$OCOR_{1g}$ group, in which $R_{1g}$ represents a linear or branched alkyl chain, preferably a $C_1$-$C_3$ alkyl chain, and more preferably a $C_1$ alkyl group; or $R_{15}$ is a carbon forming an ethylenic unsaturation with the tetrahydropyranone ring.

According to a preferred embodiment, $R_{11}$ is a —$COR_{1a}$ group, in which $R_{1a}$ is a linear or branched alkyl chain, and preferably $R_{11}$ is a —$COCH(CH_3)C_2H_5$ or —$COC(CH_3)_2C_2H_5$ group.

Advantageously, $R_{14}$ represent a $C_1$-$C_6$ alkyl chain, preferably a —$CH_3$ group, and both $R_{12}$ and $R_{13}$ represent hydrogen atoms. Alternatively, $R_{12}$ and $R_{14}$ may represent a $C_1$-$C_6$ alkyl chain, preferably a —$CH_3$ group, and $R_{13}$ a hydrogen atom.

According to another preferred embodiment, $n_1$=2, and $R_{15}$ represents a hydroxyl group.

According a preferred embodiment of the invention, the inhibitor of sterol metabolism is selected from Ethinylestradiol, Mevastatin, Simvastatin, Butenafine, Terbinafine, Estrone. The most preferred inhibitors of sterol metabolism of formula (I) are Ethinylestradiol and Estrone. The most preferred inhibitor of sterol metabolism of formula (II) is Butenafine. The most preferred inhibitors of sterol metabolism of formula (III) are Mevastatin and Simvastatin.

The inhibitors of sterol metabolism of the invention are all acting on the "mevalonate" pathway, and not on the "non-mevalonate" pathway of synthesis of sterols (see FIG. 1).

More specifically:
the inhibitors of sterol metabolism of formula (I) are acting as steroid structural analogs interacting with protein involved in sterol metabolism including Estrone (Merola and Arnold, Science, Vol. 144, 301-302 (1964)) and Ethinylestradiol (Koopen et al., Journal of Lipid Research, Vol. 40, 1999),
the inhibitors of sterol metabolism of formula (II) are acting as squalene epoxidase inhibitors (Belter et al., Biol. Chem., Vol. 392, 1053-1075 (2011)), and
the inhibitors of sterol metabolism of formula (III) are acting as HMG-CoA reductase inhibitors (Liu et al., Mol. Biol. Rep. (2010) 37:1391-1395).

Another subject-matter of the invention is a method for producing fatty acids comprising a triggering of triacylglycerols accumulation step in microalgae as defined according to the invention, followed by an extraction step of the triacylglycerols accumulated in the microalgae.

The invention also relates to a method for producing biofuels comprising the following steps:
a triggering of triacylglycerols accumulation step in microalgae as defined according to the invention, followed by
(ii) an extraction step of the triacylglycerols accumulated in microalgae during step (i), and
(iii) a trans-esterification step of the triacylglycerols recovered during step (ii), for example as described by Zhang et al., Bioresource Technology 147 (2013) 59-64.

The invention also concerns a method for producing pharmaceutical or cosmetic compositions comprising the following steps:

(i') a triggering of triacylglycerols accumulation step in microalgae as defined according to the invention, followed by
(ii') an extraction step of the triacylgycerols accumulated in microalgae during step (i'), and
(iii') a step of adding at least one pharmaceutically or cosmetically acceptable excipient to the triacylglycerols recovered during step (ii').

The invention also relates to a method for producing human food and animal feed supplements comprising the following steps:
(i") a triggering of triacylglycerols accumulation step in microalgae as defined according to the invention, followed by
(ii") an extraction step of the triacylglycerols accumulated in microalgae during step (i"), and
(iii") a step of adding at least one food additive to the triacylglycerols recovered during step (ii").

The methods of the invention may comprise one or more extraction steps after the triggering of triacylglycerols accumulation step in microalgae. The extraction step may be implemented using solvents or another extraction method well known form the skilled artisan.

Another subject-matter of the invention relates to the use of an inhibitor of sterol metabolism to accumulate triglycerides in microorganism, preferably in microalgae, more preferably in microalgae of the diatom phylum, and still more preferably in the diatom microalgae species *Phaeodactylum tricornutum*.

Advantageously, the invention concerns the use of an inhibitor of sterol metabolism selected from the compounds of formula (I), (II) and (III), such as Ethinylestradiol, Mevastatin, Simvastatin, Butenafine, Terbinafine, Estrone, to accumulate triglycerides in microorganism, preferably in microalgae, more preferably in microalgae of the diatom phylum, and still more preferably in the diatom microalgae species *Phaeodactylum tricornutum*. The invention also concerns the use of combination of inhibitors of sterol metabolism selected from the compounds of formula (I), (II) and (III), such as Ethinylestradiol, Mevastatin, Simvastatin, Butenafine, Terbinafine, Estrone, as well as their combination with other methods known to enhance the accumulation of TAG in microalgae, in particular a shortage of nutrient, and more preferably a shortage of nitrogen.

BRIEF DESCRIPTION OF THE DRAWINGS

In addition to the above provisions, the invention also comprises other provisions which will emerge from the remainder of the description which follows, and also to the appended drawings in which.

DETAILED DESCRIPTION

Examples

Figure 1:
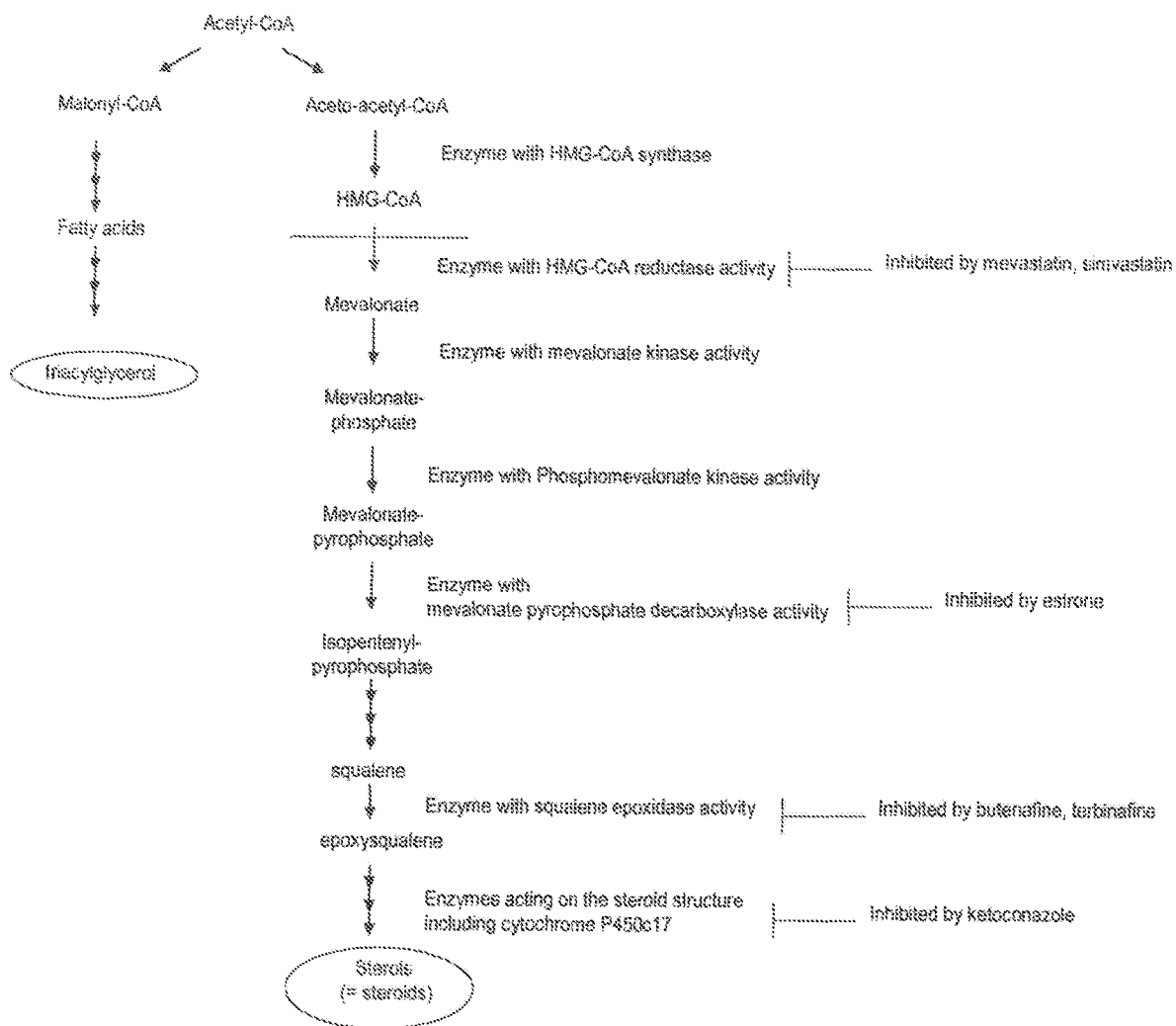
FIG. 1 gives a schematic view of the sterol biosynthetic pathway via mevalonic acid, and represents the action of Mevastatin and Simvastatin (Liu et al., Mol. Biol. Rep. (2010) 37:1391-1395), Estrone (Merola and Arnold, Science, Vol. 144, 301-302 (1964), Butenafine and Terbinafine (Belter et al., Biol. Chem., Vol. 392, 1053-1075 (2011)), FIG. 2 represents pictures of a *Phaeodactylum* cell visualized by confocal microscopy after a 72 h cultivation in Nitrogen-rich N(+) or in Nitrogen-starved N(−) medium On the left side (A and C), cells are shown in phase contrast ("phase"). On the right side (B and D), cells are shown after excitation of Nile red at 488 nm and emission at 519 nm, FIG. 3a-h illustrates the dose response for Ethinylestradiol, Mevastatin, Simvastatin and Estrone, and FIG. 4 illustrates the dose response for Ethinylestradiol, Mevastatin and Simvastatin with an evaluation of the TAG content by staining with Nile Red and an evaluation of cells by counting in an aliquote fraction using a Malassez cell, FIG. 5 shows the effect of Butenafine on Nile Red accumulation in *Nannochloropsis gaditana* grown respectively in ESAW 1N1P media and ESAW 10N10P media. Nile Red Fluorescence was normalized by calculating the relative fluorescence units per million cells, and FIG. 6 shows the effect of Ethinylestradiol on Nile Red accumulation in *Nannochloropsis gaditana* grown respectively in ESAW 1N1P media and ESAW 10N10P media. Nile Red Fluorescence was normalized by calculating the relative fluorescence units per million cells.

1) Materials & Methods 1) 1-*Phaeodactylum tricornutum* Strain and Growth Conditions

*Phaeodactylum tricornutum* (Pt1) Bohlin Strain 8.6 CCMP2561 (Culture Collection of Marine Phytoplankton, now known as NCMA: National Center for Marine Algae and Microbiota) was used in experiments.

Pt1 was grown at 20° C. in 250 mL flask using "enriched artificial seawater" (ESAW) medium, prepared following the recommendations of the Canadian Center for the Culture of Microorganisms.

To prepare the ESAW medium, four separated solutions are prepared, two solutions of salts (solutions 1 and 2), one solution of nutrients, and one solution of vitamins. Salts are added in order to distilled deionized water (DDW). When the salts in solutions 1 and 2 are completely dissolved, the solutions 1 and 2 are mixed together. The total volume is diluted with DDW.

TABLE 3

Compositions of the ESAW salts solutions 1 and 2

| | Molecular weight (g · mol⁻¹) | Amount to weight (g/L solution) | Concentration (mM) |
|---|---|---|---|
| Solution 1: Anhydrous salts | | | |
| NaCl | 58.44 | 20.756 | 362.7 |
| Na$_2$SO$_4$ | 142.04 | 3.477 | 25.0 |
| KCl | 74.56 | 0.587 | 8.03 |
| NaHCO$_3$ | 84 | 0.17 | 2.067 |
| KBr | 119.01 | 0.0845 | 0.725 |
| H$_3$BO$_3$ | 61.83 | 0.022 | 0.372 |
| NaF | 41.99 | 0.0027 | 0.0657 |
| Solution 2: Hydrated salts | | | |
| MgCl$_2$•6H$_2$O | 203.33 | 9.395 | 47.18 |
| CaCl$_2$•2H$_2$O | 147.03 | 1.316 | 9.134 |
| SrCl$_2$•6H$_2$O | 266.64 | 0.0214 | 0.082 |

TABLE 4

Nutrient Enrichment Stocks

| | Solutions | Stock concentration (g · L⁻¹) | Final concentration (μM) |
|---|---|---|---|
| 1 | NaNO$_3$ | 46.67 | 549.1 |
| 2* | Na$_2$ glycerophosphate | 6.67 | 21.8 |

TABLE 4-continued

Nutrient Enrichment Stocks

| | Solutions | Stock concentration (g · L⁻¹) | Final concentration (μM) |
|---|---|---|---|
| 3 | Na$_2$SiO$_3$•9H$_2$O | 15.00 | 105.6 |
| 4** | Na$_2$EDTA•2H$_2$O | 3.64 | 9.81 |
| | Fe(NH$_4$)$_2$(SO$_4$)$_2$•6H$_2$O*** | 2.34 | 5.97 |
| | FeCl$_3$•6H$_2$O | 0.16 | 0.592 |
| 5 | MnSO$_4$•4H$_2$O | 0.54 | 2.42 |
| | ZnSO$_4$•7H$_2$O | 0.073 | 0.254 |
| | CoSO$_4$•7H$_2$O | 0.016 | 0.0569 |
| | Na$_2$MoO$_4$•2H$_2$O | 0.126 | 0.520 |
| | Na$_2$EDTA•2H$_2$O | 1.89 | 5.05 |
| 6 | H$_3$BO$_3$ | 3.80 | 61.46 |
| 7 | NaSeO$_3$ | 0.00173 | 0.001 |

*Na$_2$ glycerophosphate can be replaced with an equimolar stock of Na$_2$HPO$_4$.
**Na$_2$EDTA•2H$_2$O is added before the trace metals Fe(NH$_4$)$_2$(SO$_4$)$_2$•6H$_2$O and FeCl$_3$•6H$_2$O.
***Fe(NH$_4$)$_2$(SO$_4$)$_2$•6H$_2$O can be replaced with an equimolar stock of FeCl$_3$.
Solution 5 is adjusted to pH = 6 with 2 g of Na$_2$CO$_3$.
Solution 4 can be heated to dissolve the iron.

TABLE 5

Vitamin Stocks

| Vitamin Stock | Stock concentration (g · L⁻¹) | Final concentration (mM) |
|---|---|---|
| Thiamine | 0.1 | $2.97 \times 10^{-1}$ |
| Vitamin B12 | 0.002 | $1.47 \times 10^{-3}$ |
| Biotin | 0.001 | $4.09 \times 10^{-3}$ |

To prepare the ESAW medium, the solutions are filtered through 0.45 μm membrane filter with a glass fiber prefilter. A flask is acid-washed in 10% HCl and rinsed in distilled water before first use. To 1 L of filtered salt solution, 1 mL of Nutrient Enrichment Stock solutions 1, 2, 4, 5, 6 and 7, 2 mL of Nutrient Enrichment Stock solution 3, and 2 mL of the Vitamin Stock are added (Tables 4 and 5). To reduce precipitation during autoclaving, 1.44 mL of 1N HCl and 0.12 g of sodium bicarbonate are added. The obtained ESAW medium is then sterilized by autoclaving.

Cells were grown on a 12:12 light (450 μEinstein-1 sec⁻¹)/dark cycle (an Einstein defined the energy in one mole ($6.022 \times 10^{23}$) of photons). Cells were sub-cultured every week by inoculate fresh media with ⅕ of previous culture. Nitrogen-rich N(+) medium contained no source of nitrogen. Nitrogen-starved N(−), medium contained 0.05 g/L NaNO$_3$. To monitor cell growth, a genetically modified strain containing a Histone H4 protein fused to the yellow fluorescent protein was used (Siaut et al., Gene 406 (2007) 23-35).

1) 2-Principle of Nile Red Staining of Oil Droplets

Accumulation of oil droplets can be monitored by Nile Red (Sigma Aldrich) fluorescent staining (Excitation wavelength at 485 nm; emission at 525 nm) as described by Ren et al. (Biotechnology for Biofuels 2013, 6:143), Cells were diluted and adjusted to a cell density that was linearly correlated with Nile Red fluorescence. Nile Red solution (40 μL of 2.5 μg·mL⁻¹ stock concentration, in 100% DMSO) was added to 160 μL cell suspension. Specific fluorescence was determined by dividing Nile Red fluorescence intensity by the number of cells. Oil bodies stained with Nile Red were then visualized using a Zeiss AxioScope.A1 microscope (FITC filter; Excitation wavelength at 488 nm; emission at 519 nm).

Figure 2:
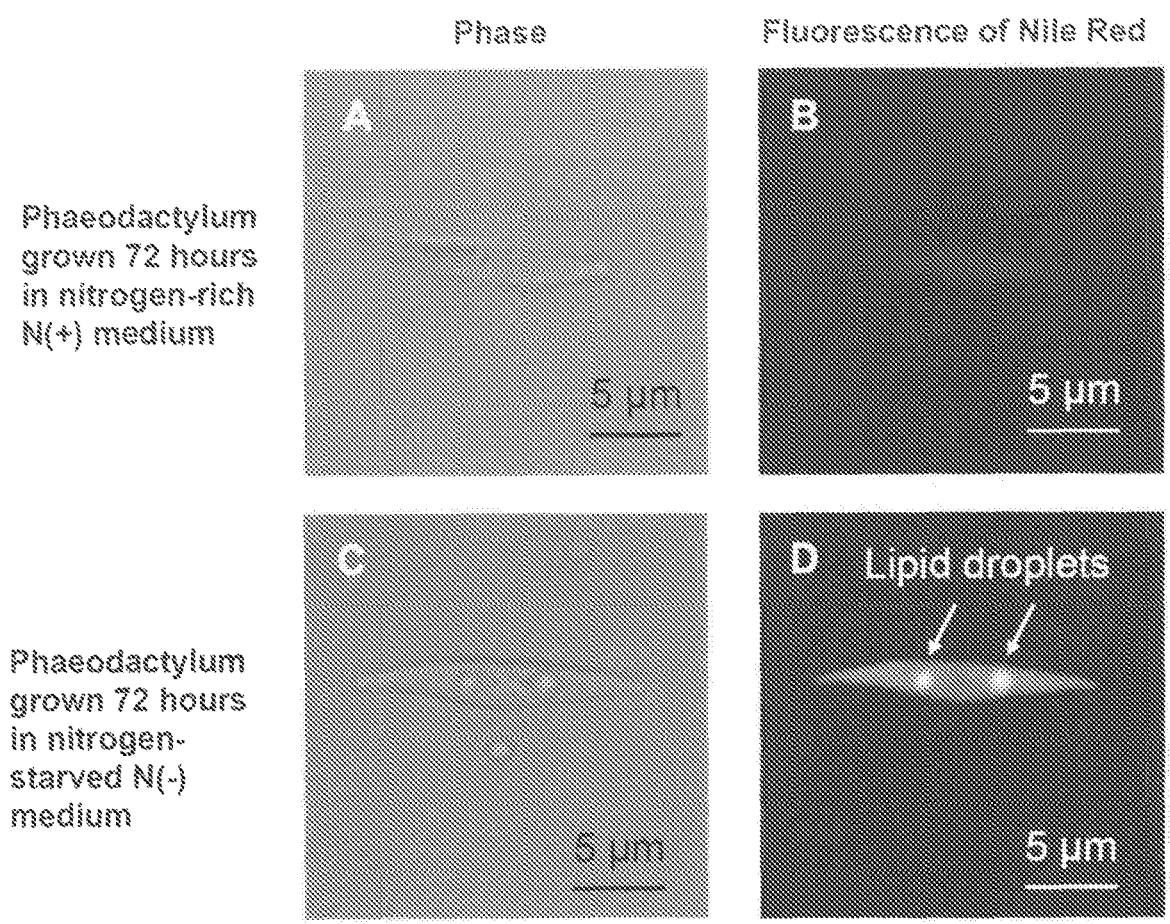
Figure 3A:
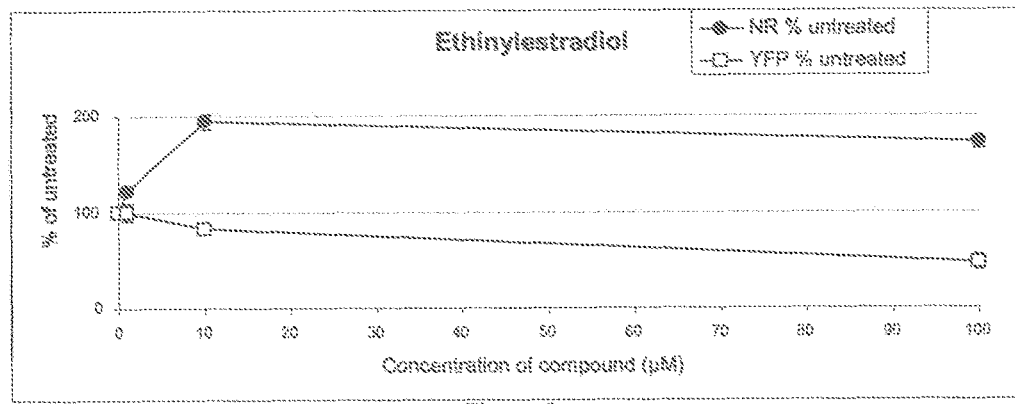
Figure 3B:
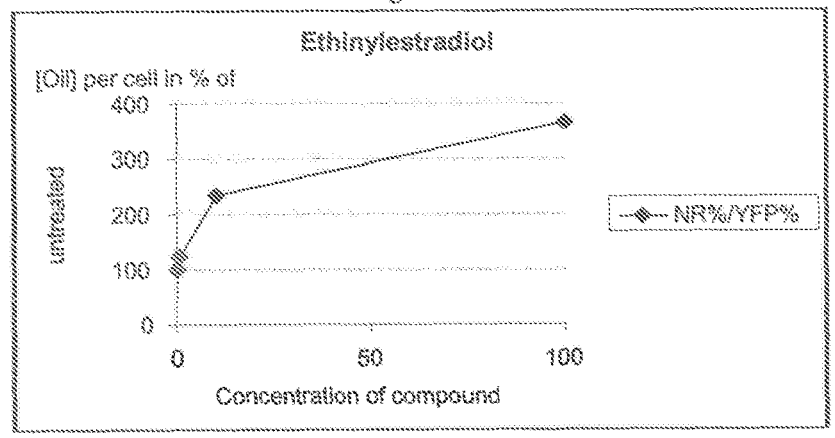
Figure 3C:
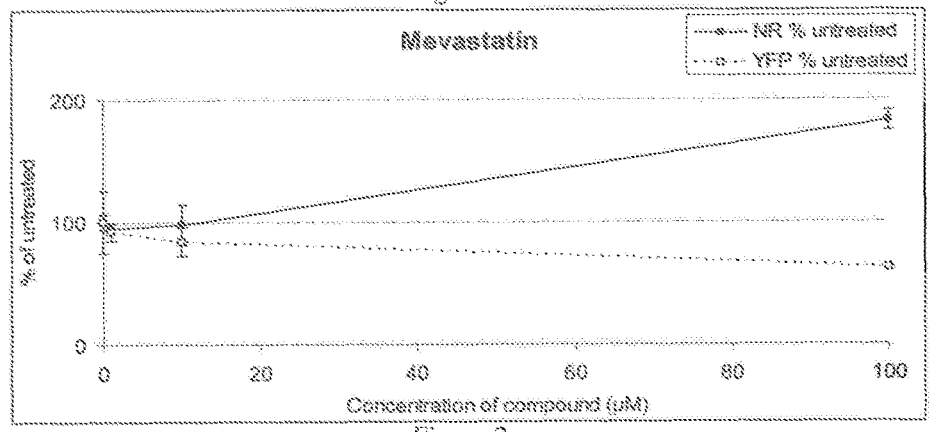
Figure 3D:
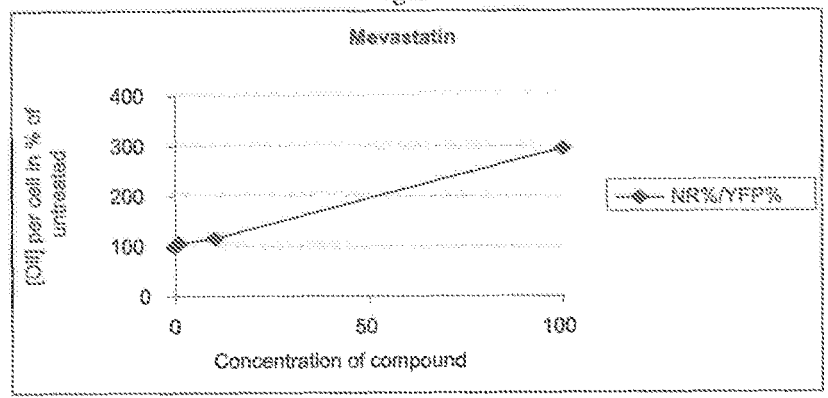
Figure 3E:
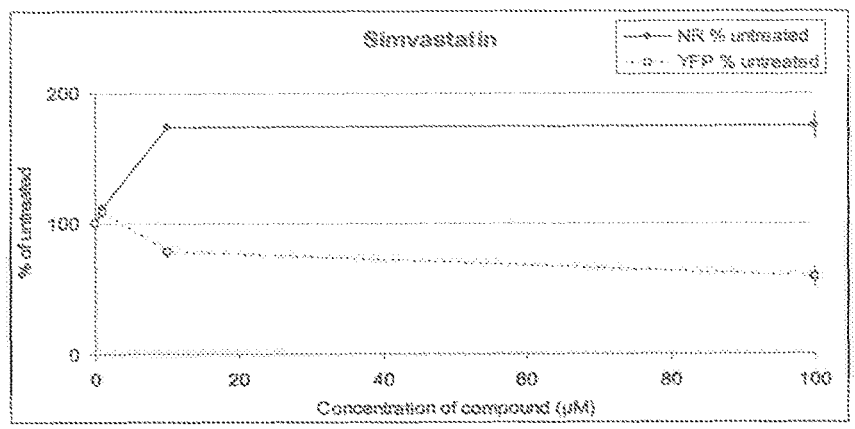
Figure 3F:
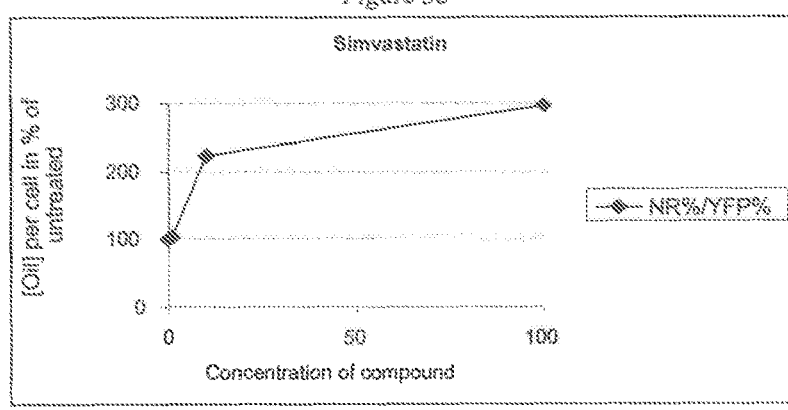
Figure 3G:
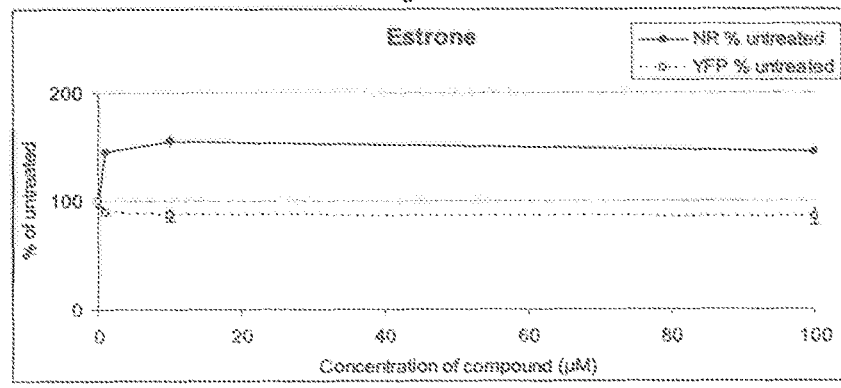
Figure 3H:
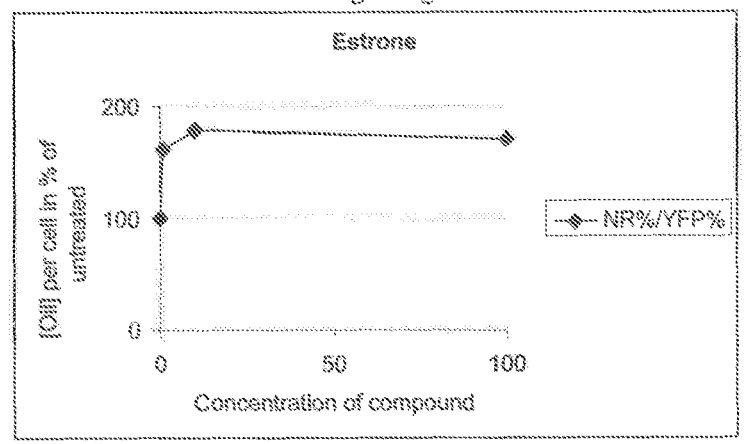

Lipid droplets can be visualized. In FIG. 2, a *Phaeodactylum* cell was visualized by confocal microscopy after a 72 h cultivation in Nitrogen-rich N(+) medium or in Nitrogen-starved N(−) medium. On the left side, cells are shown in phase contrast ("phase"). On the right side, cells are shown after excitation of Nile red at 488 nm and emission at 519 nm. Lipid droplets can be clearly visualized.

This principle was use to measure the presence of oil in *Phaeodactylum tricornutum* simply by using a spectrofluorometer (in these conditions, to lower the detection of other fluorophores within the cell, such as chlorophylls, excitation was at 530 nm and emission at 580 nm).

1) 3-Alternative Method for Oil Level Detection

Alternatively, oil is extracted using solvents or another extraction method, separated and purified by thin layer chromatography and methanolyzed to produce fatty acid methyl esters and quantified by gas chromatography coupled to a ionization flame detector or a mass spectrometer.

TAG were extracted from 200 mg of freeze-dried *Phaeodactylum tricornutum* cells in order to prevent lipid degradation. Briefly, cells were frozen in liquid nitrogen immediately after harvest. The freeze-dried cell pellet was resuspended in 4 mL of boiling ethanol for 5 minutes followed by the addition of 2 mL of methanol and 8 mL of chloroform at room temperature. The mixture was then saturated with argon and stirred for 1 h at room temperature. After filtration through glass wool, cell remains were rinsed with 3 mL of chloroform/methanol (2:1, v/v). In order to initiate biphase formation, 5 mL of NaCl 1% was then added to the filtrate. The chloroform phase was dried under argon before re-solubilization of the lipid extract in pure chloroform. To isolate TAG, lipids were run on silica gel thin layer chromatography (TLC) plates (Merck) with hexane/diethylether/acetic acid (70:30:1, v/v). Lipids were then visualized under UV light after pulverization of 8-anilino-1-naphthalenesulfonic acid at 2% in methanol. They were then scraped off from the TLC plates for further analyses. For acyl profiling and quantification of TAG, fatty acids were methylated using 3 mL of 2.5% $H_2SO_4$ in methanol during 1 h at 100° C. (including standard amounts of 21:0). The reaction was stopped by the addition of 3 mL of water and 3 mL of hexane. The hexane phase was analyzed by gas liquid chromatography (Perkin Elmer) on a BPX70 (SGE) column. Methylated fatty acids were identified by comparison of their retention times with those of standards and quantified by surface peak method using 21:0 for calibration. Extraction and quantification were done at least 3 times.

1) 4-Principle of Cell Normalization

The number of cells in a sample can be evaluated using a fluorescent reporter, like the strain by Siaut et al. (Gene 406 (2007) 23-35) containing a genetic construction with Histone H4 protein fused to the Yellow Fluorescent Protein (YFP) (FIG. 5A of Siaut et al., Gene 406 (2007) 23-35).

For cell counting, we can either use this strain called "ptYFP" and measure the fluorescence emitted by the YFP at 530 nm after excitation at 515 nm, or use any strain and estimate cell numbers by counting with a Malassez grid (supplier: Mareinfeld).

1) 5-Incubation of *Phaeodactylum tricornutum* with Inhibitors of the Sterol Metabolism and Detection of Oil Accumulation Triggered by the Treatment On the first day, we prepared 48 well plates by adding 4 mm glass beads sterilized with Ultra-Violet exposure in each well.

We prepared fresh suspensions of microalgae in exponential growth phase. For cell normalization based on YFP fluorescence, cells of *Phaeodactylum tricornutum* containing a YFP reporter (ptYFP) cultured in N(+) ESAW medium were centrifuged at 3,500 rpm, 5 min. For cell normalization based on counting using a Malassez grid, cells of the Pt1 strain of *Phaeodactylum tricornutum* cultured in N(+) ESAW medium were centrifuged at 3,500 rpm, 5 min. The supernatant was discarded and the pellet suspended in N(−) ESAW. The microalgae were then centrifuged at 3,500 rpm, 5 min. The supernatant was discarded and the pellet suspended in N(−) ESAW. Cells were then diluted to $1 \times 10^6$ cells/mL in N(−) ESAW. Samples were then separated into two batches. One was supplemented with 1 µL/mL of 46.7 g/L $NaNO_3$ stock to obtain a suspension of cells in N(+) ESAW medium. Another was left without $NaNO_3$ to obtain a N(−) ESAW culture as a control for high lipid accumulation. In a 48-well clear NUNC plate, 450 µL/well of $1 \times 10^6$ cells/mL were dispensed.

For a dose-response analysis, each well of the 48-well plate was then subjected to an appropriate incubation with 0, 1, 10 or 100 µM of inhibitor of sterol metabolism using 50 µL of the following: 50 µL of a 10 time concentrated solution of inhibitor of sterol metabolism (5% DMSO:95% N(+) ESAW) or 50 µL of Nitrogen-rich medium without any inhibitor of sterol metabolism (5% DMSO:95% N(+) ESAW) or Nitrogen-starved medium without any inhibitor of sterol metabolism (5% DMSO:95% N(−) ESAW) as a positive control.

For an analysis of the effect of a single dose, an incubation was performed with 0, and a chosen concentration of inhibitor of sterol metabolism (50 µM).

In all cases, the edge of the plate was sealed using a parafilm. Plates were incubated for 48 h in an incubator with top lighting, 20° C., 100 rpm, 12 h/12 h light/dark.

After an incubation of 48 hours, fluorescence was measured at the following excitation/emission wavelengths, 530/580 nm (to evaluate a baseline fluorescence prior Nile Red addition) and 515/530 nm (to evaluate YFP fluorescence). Following this first measure, 40 µL of Nile Red (2.5 µg/mL stock concentration, in 100% DMSO) are added. Plates are mixed and incubated 20 minutes at room temperature, protected from light. Nile Red fluorescence is then measured using a spectrofluorometer (excitation 530 nm/emission 580 nm).

1) 6-Incubation of *Nannochloropsis gaditana* with Inhibitors of the Sterol Metabolism and Detection of Oil Accumulation Triggered by the Treatment Experiments were performed in two different conditions of *Nannochloropsis gaditana*: cells were either cultured in ESAW containing 47 mg·$L^{-1}$ $NaNO_3$ and 3 mg·$L^{-1}$ $NaH_2PO_4$ (medium 1N1P), or 470 mg/L $NaNO_3$ and 30 mg·$L^{-1}NaH_2PO_4$) (medium 10N10P). Cells in an exponential growth phase were collected via centrifugation at 3500 rpm for 10 minutes. The supernatant was discarded and the cells were resuspended in the same volume of ESAW medium (either 1N1P or 10N10P). The cultures were centrifuged again at 3500 rpm, for 10 minutes, and the supernatant was discarded. The pellet was resuspended in ESAW (either 1N1P or 10N10P) to obtain a concentration of $2 \times 10^6$ cells/mL. Cell counts were performed using a Malassez counting chamber, allowing 10 minutes for the cells to settle before counting.

Twenty milliliters of $2 \times 10^6$ cells/mL of *Nannochloropsis gaditana* in ESAW (10N10P) and ESAW (1N1P) were dispensed into sterile glass conical flasks. Stocks of inhibitor of sterol metabolism were prepared in DMSO. Inhibitors of sterol metabolism were added to the 20 mL *Nannochloropsis gaditana* samples at final concentrations of 10 µM, 30 µM, or 100 µM. The maximum final concentration of DMSO in the samples was 1% (v/v), All cultures were incubated for seven days at 100 rpm, 12 h/12 h light/dark cycle, 50 $\mu E \cdot m^{-2} \cdot s^{-1}$, 20° C.

Each day, an aliquot was taken from each flask in order to perform a Nile Red stain and cell counts. 160 µL per sample was added to black 96 well plates, and allowed to settle for 10 minutes. In order to detect any background noise, fluorescence was measured at excitation and emission of 530 nm and 580 nm, respectively. 40 µL of 2.5 µg·mL$^{-1}$ Nile Red in DMSO was added to each well, and mixed thoroughly. After 20 minutes of incubation, Nile Red fluorescence was measured at excitation and emission of 530 nm and 580 nm, respectively.

Nile Red Fluorescence was normalized by calculating the relative fluorescence units per million cells. Results were expressed as a percentage of Nile Red fluorescence of *Nannochloropsis gaditana* cultured in complete medium (either ESAW (10N10P) or ESAW (1N1P)).

1) 7-Inhibitors of Sterol Metabolism

Inhibitors of sterol metabolism were obtained from the Prestwick library for their ability to trigger the accumulation of lipid droplets within the cells of *Phaeodactylum tricornutum*, and then purchased from Sigma-Aldrich,

TABLE 6

Inhibitors of sterol metabolism selected from the Prestwick library

| Chemical name | Structure | Molecular Formula |
|---|---|---|
| Mevastatin | 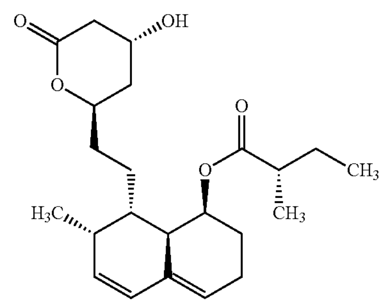 [SMILES: CC[C@H](C)C(=O)O[C@H]1CCC=C2C=C[C@H](C)[C@H](CC[C@@H]3C[C@@H](O)CC(=O)O3)[C@H]21] | $C_{23}H_{34}O_5$ |
| Butenafine | 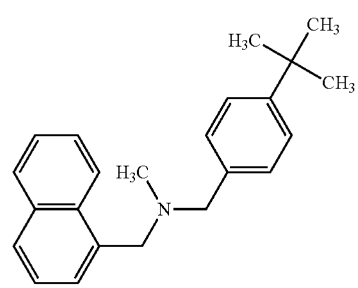 [SMILES: CN(Cc1ccc(C(C)(C)C)cc1)Cc1cccc2ccccc12] | $C_{23}H_{27}N$ |
| Simvastatin | 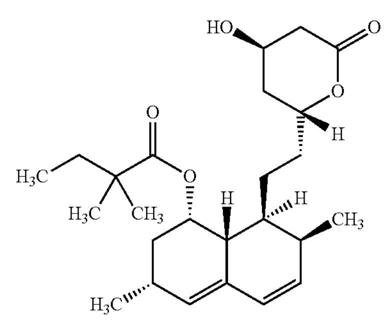 | $C_{25}H_{38}O_5$ |
| Estrone | 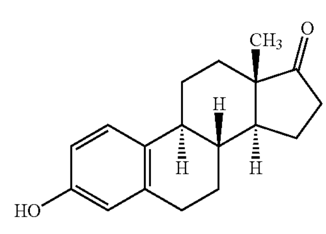 | $C_{18}H_{22}O_2$ |

TABLE 6-continued

Inhibitors of sterol metabolism selected from the Prestwick library

| Chemical name | Structure | Molecular Formula |
|---|---|---|
| Ethinylestradiol | 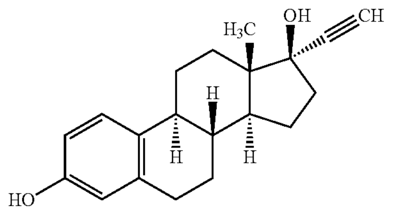 | $C_{20}H_{24}O_2$ |

2) Results

*Phaeodactylum tricornutum* was incubated for 48 h in presence of 10 µM of Mevastatin, Butenafine, Simvastatin, Estrone, Ethinylestradiol and Terbinafine.

In all cases the presence of oil per cell increased by a factor of at least 1.5, based on Nile Red staining.

FIG. 3a-h illustrates the dose response for Ethinylestradiol, Mevastatin, Simvastatin and Estrone with an evaluation of the TAG content by staining with Nile Red, and an evaluation of cells by monitoring YFP fluorescence from an expressed Histone H4 reporter gene. On the left, FIG. 3a-h shows the Nile Red levels in percent of untreated cells and the number of cells estimated by the YFP fluorescence expressed in percent of untreated cells. The right panels show the increase of oil content per cell, by the ratio of Nile Red fluorescence/YFP fluorescence, expressed in percent of untreated cells. The oil content per cell increases with drug concentration and consequently level of sterol metabolism inhibition and ranges from 120 to 400% when compared to untreated cells.

Figure 4:
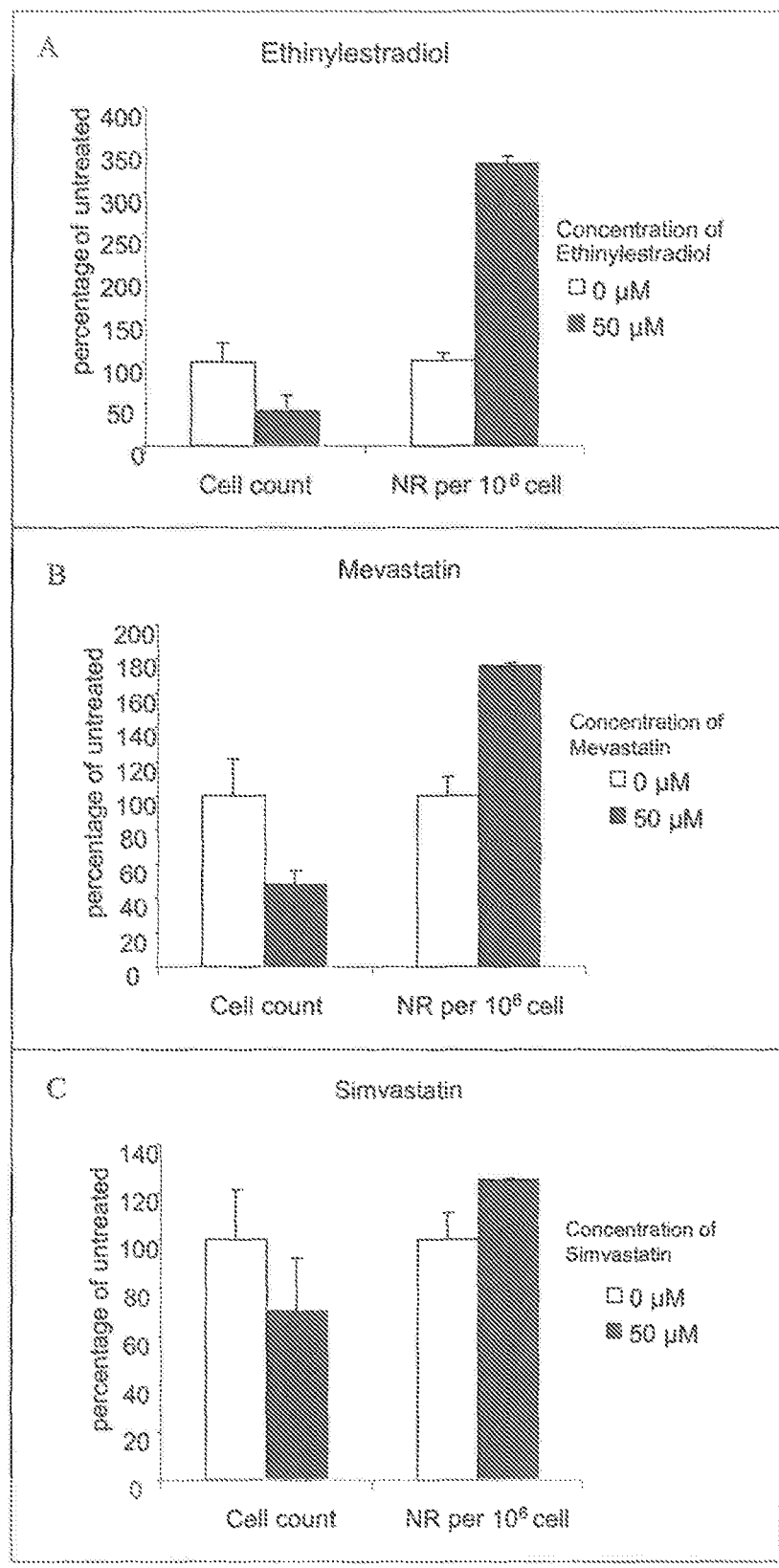

FIG. 4 illustrates the dose response for Ethinylestradiol (A), Mevastatin (B) and Simvastatin (C) with an evaluation of the TAG content by staining with Nile Red and an evaluation of cells by counting in an aliquote fraction using a Malassez cell. In histograms of FIG. 4, the white bars indicate the evaluation of cell numbers in percent of untreated cells, and the black bars indicate the Nile Red per $10^6$ cell, in percent of untreated cells. The oil content per cell, and consequently level of sterol metabolism inhibition, increases with incubation of 50 µM of inhibitor, and ranges from 120 to 350% when compared to untreated cells.

*Nannochloropsis gaditana* was incubated in presence of Butenafine and
Ethinylestradiol.

Figure 5:
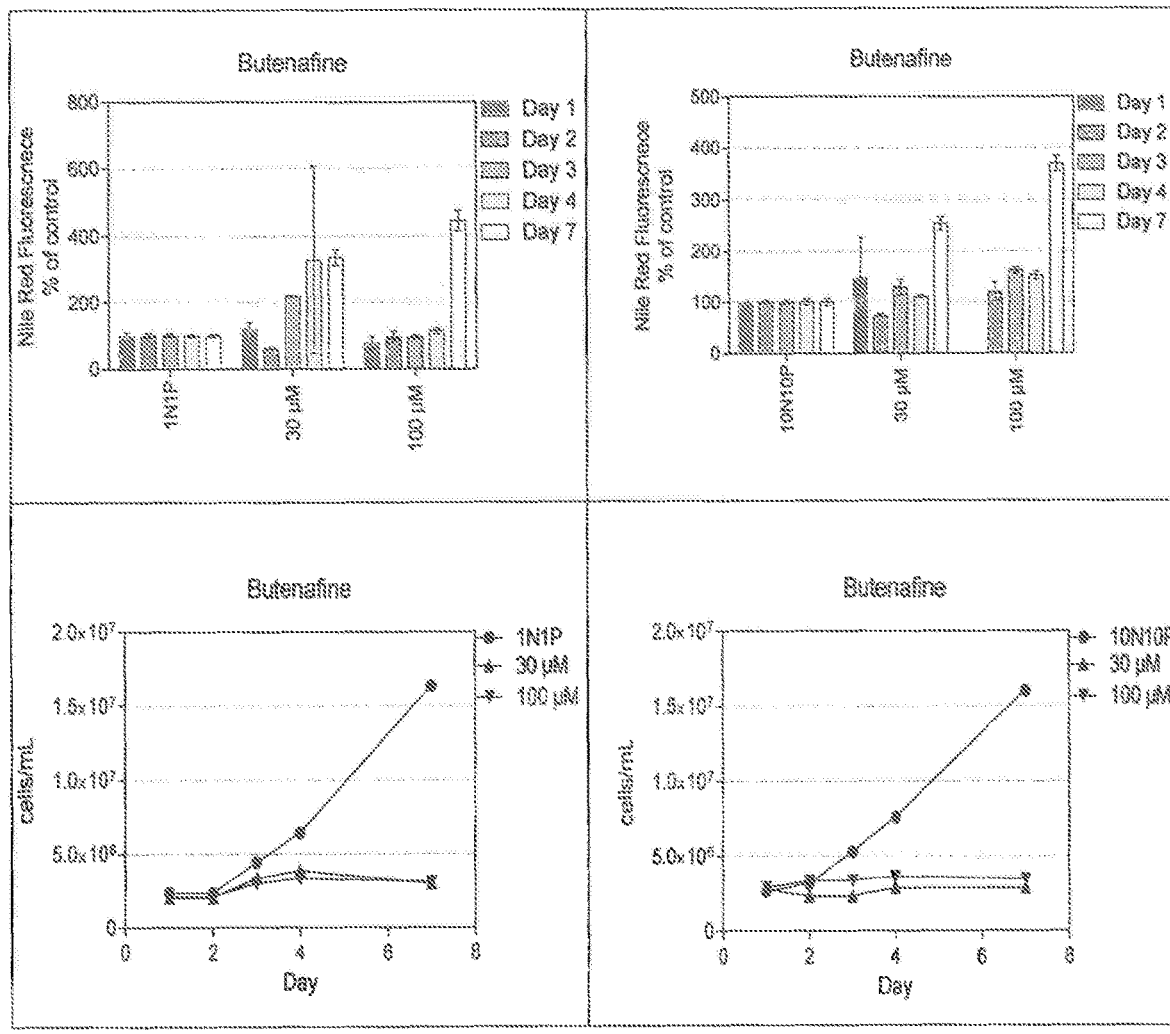
Figure 6:
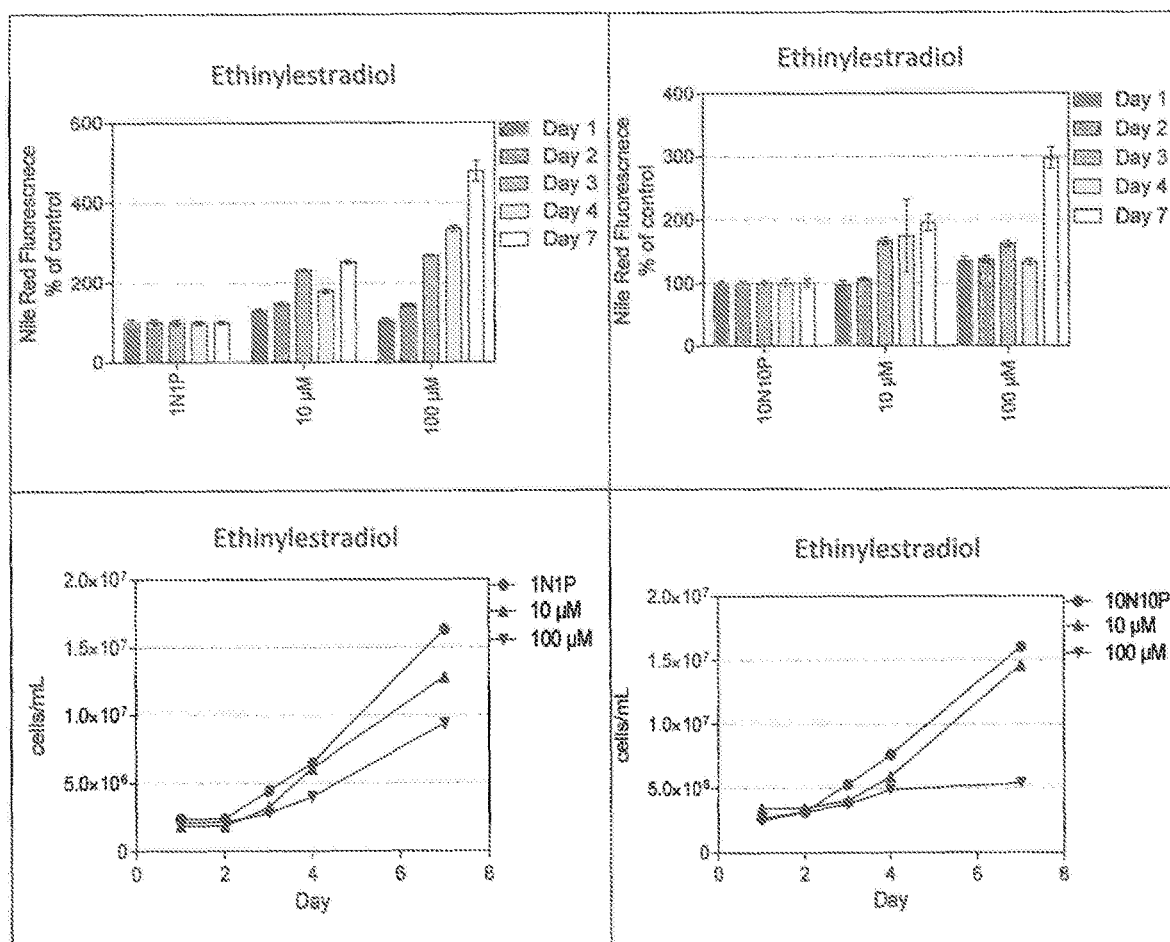

FIGS. 5 and 6 illustrate the effect of Butenafine and Ethinylestradiol on Nile Red accumulation in *Nannochloropsis gaditana* grown respectively in ESAW 1N1P media and ESAW 10N10P media. Nile Red Fluorescence was normalized by calculating the relative fluorescence units per million cells.

Both Butenafine and Ethinylestradiol trigger the accumulation of oil in *Nannochloropsis gaditana*, in different media and with a time course that can be observed at least for 7 days.

The invention claimed is:

1. A method for triggering triacylglycerols accumulation in microalgae by inhibiting the sterol metabolism, wherein the method comprises a step of incubating the microalgae with an inhibitor of sterol metabolism, said inhibitor being a compound of formula (I) or a salt thereof:

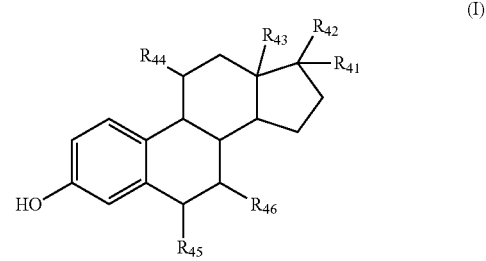

(I)

wherein:
R$_{41}$ and R$_{42}$, identical or different, represent a hydrogen atom, alkyl, alkenyl, alkynl, or hydroxyl, —COR$_{4a}$ or COOR$_{4a}$ group, in which R$_{4a}$ represents a hydrogen atom, a linear or branched alkyl, aryl, heteroaryl group, optionally substituted with one or more groups independently selected from alkyl or cycloalkyl groups, or R$_{41}$ and R$_{42}$ form together an oxygen atom attached by a double bond;

R$_{43}$ represents a hydrogen atom, or an alkyl group; and

R$_{44}$, R$_{45}$ and R$_{46}$, identical or different, represent a hydrogen atom, an alkyl, alkoxy, hydroxyl group, or an oxygen atom attached by a double bond, said alkyl group being optionally substituted with one or more halogen atoms, and including optionally in its chain one or more sulfoxide functions, wherein the concentration of the inhibitor of sterol metabolism ranges from 1 µM to 1M, and wherein the microalgae is selected from the group consisting of diatom microalgae species *Phaeodactylum tricornutum* and the Chromalveolata microalgae species *Nannochloropsis gaditana*.

2. A method according to claim 1, wherein the incubation step is implemented in a nitrogen medium.

3. A method according to claim 1, wherein the inhibitor of sterol metabolism is selected from the group consisting of Ethinylestradiol and Estrone.

4. A method for producing fatty acids comprising a triggering of triacylglycerols accumulation step in microalgae as defined according to claim 1.

5. A method for producing biofuels comprising the following steps;
 (i) a triggering of triacylglycerols accumulation step in microalgae as defined according to claim 1, followed by
 (ii) an extraction step of the triacylglycerols accumulated in microalgae during step (i), and
 (iii) a trans-esterification step of the triacylglycerols recovered during step (ii).

6. The method according to claim 1, wherein the concentration of the inhibitor of sterol metabolism ranges from 5 µM to 1M.

7. The method according to claim 1, wherein the concentration of the inhibitor of sterol metabolism ranges from 5 to 20 µM.

\* \* \* \* \*